United States Patent
Keldmann et al.

(10) Patent No.: US 6,648,848 B1
(45) Date of Patent: Nov. 18, 2003

(54) INHALER FOR POWDERED MEDICAMENTS

(75) Inventors: Erik Keldmann, Odense (DK); Troels Keldmann, København (DK); Ricardo Palacios Pelaez, Bilbao (ES); Jorge Martinez Ouesada, Bilbao (ES)

(73) Assignee: Direct-Haler A/S, Odense (DK)

( * ) Notice: Subject to any disclaimer, the term of this patent is extended or adjusted under 35 U.S.C. 154(b) by 0 days.

(21) Appl. No.: 09/424,085

(22) PCT Filed: May 26, 1998

(86) PCT No.: PCT/DK98/00214

§ 371 (c)(1),
(2), (4) Date: Jan. 12, 2000

(87) PCT Pub. No.: WO98/53869

PCT Pub. Date: Dec. 3, 1998

(30) Foreign Application Priority Data

May 27, 1997 (DK) ................................. 606/97

(51) Int. Cl.⁷ ............................................... A61M 31/00
(52) U.S. Cl. ...................................................... 604/57
(58) Field of Search ........................... 604/57, 58, 59, 604/60, 61, 62, 63, 64, 48; 128/203.15, 203.16, 203.17, 203.18, 203.19, 203.2, 203.21, 203.22, 203.23

(56) References Cited

U.S. PATENT DOCUMENTS

| | | | | |
|---|---|---|---|---|
| 419,942 A | * | 1/1890 | Harding .................. | 128/203.15 |
| 429,321 A | * | 6/1890 | Ramey et al. .......... | 128/203.18 |
| 658,436 A | * | 9/1900 | Groth ..................... | 128/203.18 |
| 707,445 A | * | 8/1902 | McCulloch ............. | 128/203.18 |
| 723,738 A | * | 3/1903 | Schulte ................... | 128/203.18 |
| 746,749 A | * | 12/1903 | Seidel ..................... | 128/203.18 |
| 781,428 A | * | 1/1905 | Hutchins et al. ........ | 128/203.18 |
| 794,641 A | * | 7/1905 | Ramey .................... | 128/203.18 |
| 867,827 A | * | 10/1907 | McCulloch ............. | 83/767 |
| 902,832 A | * | 11/1908 | Philbrook ............... | 128/203.18 |
| 1,375,325 A | * | 4/1921 | Schaefer ................. | 128/203.18 |
| 1,540,274 A | | 6/1925 | Moore | |
| 2,021,332 A | | 11/1935 | Silten | |
| 2,086,588 A | * | 7/1937 | Tobin et al. ............ | 128/203.18 |
| 4,216,768 A | | 8/1980 | Jack ....................... | 128/203.15 |
| 4,265,236 A | | 5/1981 | Pacella ................... | 128/203.23 |
| 5,046,493 A | * | 9/1991 | Kropkowski et al. .. | 128/203.15 |
| 5,373,841 A | * | 12/1994 | Kyllonen et al. ....... | 128/203.18 |
| 6,019,100 A | * | 2/2000 | Alving et al. ........... | 128/203.12 |
| 6,074,673 A | * | 6/2000 | Guillen ...................... | 264/4.32 |

FOREIGN PATENT DOCUMENTS

| | | |
|---|---|---|
| EP | 695 561 A1 | 2/1996 |
| GB | 2 270 293 | 3/1994 |
| WO | 96/22802 | 8/1996 |

\* cited by examiner

*Primary Examiner*—Teresa Walberg
*Assistant Examiner*—Daniel Robinson
(74) *Attorney, Agent, or Firm*—Abelman, Frayne & Schwab

(57) ABSTRACT

A method and device for introducing a powdered or particulate substance into a person's nostril

A device for applying a powdered or particulate substance to a mucous membrane in a nostril comprises a tubular body (10) similar to a drinking straw. The tubular body has opposite end parts forming a mouthpiece (11) and a nasal piece (12) to be inserted between the lips and into the nostril, respectively, of a user. The mouthpiece (11) and the nasal piece (12) are interconnected by a bent or a bendable, preferably corrugated part (13). A dose of a powdered or particulate substance arranged within the tubular body (10) is transferred to the nostril when the user blows into the mouthpiece (11). A part of the mouthpiece is preferably deflated or compresses between a pair of fingers (35) of the user. The compressed part (34) is released when the user has started to blow forcefully into the compressed mouthpiece part which is thereby inflated. It has been found that the user will automatically close the connection between the nostrils and the throat by the uvula when blowing.

8 Claims, 7 Drawing Sheets

INHALER FOR POWDERED MEDICAMENTS

A method and device for introducing a powdered or particulare substance into a person's nostril The present invention relates to a method for introducing a powdered or particulate substance into a persons nostril or nostrils. It is known to disperse the powdered or particulate substance in an air flow which is created by compressing a rubber bulb arranged at one end of a tube or hose having an opposite free end, which may be inserted into the nostril.

The present invention provides such method for introducing a powdered or particulate substance into a persons nostril or nostrils, said method comprising arranging a dose of the substance within an inner cavity of a tubular body, inserting a first open end of the tubular body communicating with the inner cavity between the persons lips, inserting a second open end of the tubular body communicating with the inner cavity into said nostril, and blowing into the first open end of the tubular body so as to create a flow of air through the inner cavity of the tubular body for transferring the substance to the nostril.

In the method according to the invention the person or patient being treated is creating the necessary air flow through the inner cavity of the tubular member by means of her/his expiratory blow. It has been found that the user will automatically close the connection between the nostrils and the throat by the uvula when blowing. Therefore, the powdered or particulate substance is substantially prevented from penetrating into the users trachea and gullet. Therefore, by using the method according to the invention almost the total amount of the substance blown into the nostril is applied to the mucous membrane within the nostril.

The method according to the invention may be carried out by means of a tubular body which has or may be given such a shape that one open end thereof may be inserted between the users lips while the opposite open end is inserted into the users nostril. The said second or opposite end of the tubular body may be bifurcated so as to form a pair of adjacent open ends which may be inserted into the users nostrils.

Prior to inserting the opposite ends of the tubular body into the mouth and the nostril, respectively, a suitable dose of any kind of a suitable type of an active substance is inserted into the inner cavity of the tubular body. This substance may for example be a substance or vaccine active against allergic reactions, such as allergy against pollen, animal hair, etc. Such substance or vaccine may be composed to the individual user. The substance may, alternatively, be any pharmaceutical or other product which is to be applied to the mucous membrane within a nostril, such as an antihistamine.

When a user or patient is about to insert the first open end of the tubular body into his or her mouth the patient's respiration may cause that the first open end of the tubular body is unintentionally exposed to a light suction or over pressure. This may cause unintentional movement of the powdered or particulate substance within or out from the tubular body. The risk of such unintentional movement of the powdered substance may be diminished when at least one venting opening is defined in the tubular body wall at or adjacent to said first open end. However, when the user or patient has inserted the first open end between the lips and is ready to blow through the tubular body the venting opening will be covered by the lips or be located within the oral cavity of the user.

At least one cross-sectional restriction may be formed in the inner cavity of the tubular body such that the dose of powdered or particulate substance is arranged downstream of the restriction in relation to the direction of the air flow transferring the powdered or particulate substance to the nostril. Such cross-sectional restriction will encourage the patient or user to blow more forcefully into the tubular body. Furthermore, the velocity of the air flow in the gorge or throat defined by the restriction will be relatively high which may assist in obtaining a good dispersion of the powdered or particulate substance in the air flow. When a venting opening as well as a restriction are formed at or adjacent to the open first end of the tubular body the restriction is preferably arranged downstream of the venting opening.

When used in a method according to the invention the efficiency of the tubular body may be further increased by defining the restriction by yieldable restriction means which are moveable between a first restricting position and a second position in which the restriction defined by the restriction means is substantially less. Such yieldable restriction means may yield and move from the first restricting position to the second non-restricting or less restricting position when the pressure difference between the inner cavity upstream of the restriction means and downstream of the restriction means or outside the tubular body has obtained a predetermined value. This means that a sudden forceful airflow may be created within the inner cavity of the tubular body when the restriction means are moving from their first to their second position.

The present invention also relates to a device for applying a powdered or particulate substance to a mucous membrane within a nostril of a user of the device, said device comprising a tubular body defining an inner flow passage extending longitudinally between a nasal piece ((12) at a first end of the tubular body to be inserted into the nostril of the user and an opposite second end of said body, and the device according to the invention is characterised in that the second end of the tubular body defines a mouthpiece to be inserted between the lips of the user, the length and the shape of the tubular body being such that the nasal piece and the mouthpiece may at the same time be positioned in the nostril and between the lips, respectively, of the user, whereby the user may blow into the mouthpiece end of the flow passage and transfer powdered or particulate substance arranged within the flow passage of the tubular body to the nostril in a dispensed condition.

The tubular body may have any suitable shape allowing the mouthpiece and the nasal piece to be correctly inserted into the mouth and nostril, respectively, of the user.

This may, for example, be obtained when the tubular body comprises an intermediate bent or bendable section. This means that the tubular body may have or may be given an angular shape. As an example, the tubular body or at least an intermediate part thereof may be made from a deformable or flexible material. Alternatively, the bent and/or bendable section may comprise adjacent, peripherally extending corrugations allowing the tubular body to be bent even when it is made from a relatively stiff material. It has been found that the inner troughs and ridges of the corrugations extending transversely to the air flow promote atomization of the particulate substance and the dispersion of the substance in the air flowing through the air flow passage. This effect is improved when the corrugations have a substantially serrated outline when viewed in a longitudinal, axial section. This means that the bottoms of the corrugation troughs and the peaks of the corrugation ridges are relatively sharp.

The device according to the invention is preferably of the disposable type. Therefore, the device may comprise a dose of a powdered or particulate substance arranged within the flow passage. When the device has been used once and the substance has been transferred to the mucous membrane of a nostril or the nostrils of a person, the device may be discarded. The said substance may be of any type which could advantageously be introduced into a nostril dispersed in an air flow, such as a substance or vaccine active against allergy, a pharmaceutical or a medicament.

When the tubular body contains a dose of the powdered or particulate substance, the opposite free ends of the mouthpiece and the nasal piece, respectively, are preferably sealed or closed by closure means, which are to be removed or opened prior to use of the device. Such closure means may be a membrane which could be removed or ruptured. In the preferred embodiment, however, the closure means comprise at least one cap member removably arranged on the free ends of the mouth piece and the nasal piece, respectively. Thus, the tubular body may be closed by means of a closure cap arranged at each of its opposite ends. However, when the tubular body has an intermediate bendable section, the mouthpiece and the nasal piece may coextend and have their free ends positioned closely adjacent prior to use of the device. This means that the tubular body may be substantially U-shaped, and the closely adjacent free ends may then be closed by a common interval cap member.

The inner and outer cross-sections of the tubular body may vary along the length of the tubular body. In the preferred embodiment, however, the tubular body has a substantially uniform inner and outer cross-sectional shape along its length. Thus, the device according to the invention may be made very simple and may be formed similar to a drinking straw.

In order to obtain a good dispersion of a particulate or powdered substance in the air flowing through the air flow passage the velocity of the air must be relatively high. Therefore, the flow passage of the tubular body preferably has a cross-sectional area not exceeding 75 mm$^2$ and preferably not more than 70 mm$^2$. In a preferred embodiment the cross-sectional areas of the flow passage do not exceed 50 mm$^2$ and are preferably 7–35 mm$^2$ or about 20 mm$^2$.

The device according to the invention may further comprise at least one venting opening defined in the tubular body at or adjacent to said first end. The device according to the invention may further comprise restriction means forming at least one cross-sectional restriction within the inner cavity of the tubular body, and a dose of powdered or particulate substance may then be arranged downstream of said restriction means before the device is used. This means that air flowing through the tubular body when a user is blowing through the mouthpiece thereof will pass the restriction means before passing the dose of powdered or particulate substance.

As explained above the restriction means are preferably yieldable so as to moveable between a first restriction position and a second non-restricting or less restricting position. Such yielding restriction means may comprise a flap which in said first position covers at least part of the cross-section of the inner cavity of the tubular body and which may be deflected and moved to a less restricting position. Alternatively, the yielding restriction means may comprise a one-way valve of any kind having a valve body which is biassed towards a closed or restricting position and which may be moved to an open or less restricting position when the biassing force is overcome by a pressure generated at the open first end or mouthpiece of the tubular body when a user or patient is blowing therein. The valve body of the one-way valve may be in the form of a flap or the like.

Preferably, the device according to the invention does not comprise parts which are separate from the tubular body because such separate parts would not only increase the manufacturing costs of the device according to the invention, but would also involve a risk to the user. Therefore, the flap, whether forming part of a one-way valve or not, is preferably an integral part of the tubular body wall. This may, for example, be obtained when the flap is cut from the tubular body wall and bent inwardly into the inner cavity of the tubular body so as to define a venting opening immediately upstream of the flap. The opening is preferably formed at or immediately adjacent to the mouthpiece so that the opening may be covered by the lips of the user or be located within the oral cavity of a user blowing through the tubular body.

Alternatively, the flap may extend into the inner cavity or into the open end of the tubular body from the free edge of the mouthpiece.

In the preferred embodiment, however, the restriction means comprise inwardly compressible or pinchable parts of the tubular body wall. Such compressible wall parts may be longitudinal sections of the tubular body having a smaller wall thickness and/or are made from a softer or more elastic material than the remaining part of the tubular body. In the preferred embodiment, however, the wall of the tubular body has substantially the same characteristics along the total length of the tubular body. In such case the tubular body may be compressible along its total length and the “compressible parts” or “pinchable parts” may be marked, for example by means of a different colour, printing, knurling, roughening, or the like, or the “compressible parts” may be defined by weakening lines, or the like. When a user or patient is using the preferred embodiment of the device according to the invention for transferring a powdered or particulate substance into his nostril or nostrils he may grip the “compressible parts” of the tubular body between his thumb and indexing finger and compress, pinch, or deflate such parts. When the user has inserted the nasal piece of the device into his nostril and placed the mouthpiece between his lips he may blow forcefully into the mouthpiece to build up a high pressure therein. Then he may release the compressible parts whereby the compressed parts are suddenly inflated and expanded so that the air may flow freely through the unobstructed inner cavity of the tubular body. The pressure being established within the oral cavity when the user is blowing while the compressible parts are deformed causes the uvula to efficiently close the connection between the nostrils and the throat.

It should be understood that the restriction means may comprise any other kind of means adapted to move from their first restricting position to their second less restricting or non-restricting position when a user is blowing into the first end of the tubular body so as to create a pressure difference between said first and second end of the tubular body exceeding a predetermined value.

The method and device according to the invention may also be used for introducing a gel-like substance into a nostril. This means that the powdered or particulate substance may be replaced by such gel-like active substance.

The invention further provides a device for dispersing a powdered or particulate substance in an airflow, said device comprising a tubular body defining a flow passage therein and a dose of powdered or particulate active substance arranged within the flow passage, the tubular body having a mouthpiece at one end to be inserted between the lips of a user so that the user may blow into or inhale through the mouthpiece end of the flow passage so as to disperse said dose of powdered or particulate substance into the air flowing through the flow passage, and the device according to the invention is characterised in that cross-sectional restriction means are arranged within the flow passage upstream of the dose of active substance moveable between a first closing or restricting position and a second position in which no or substantially less restriction is defined by the restriction means, the restriction means being adapted to move from their first restricting position to their second, less restricting position when a user is blowing into the mouthpiece end of the tubular body so as to create a pressure difference between said mouthpiece and nasal piece ends of the tubular body exceeding a predetermined value. Such device may be used not only for transferring powdered or particulate product to a nostril, but also as an inhaler. The tubular body and the restriction means may be of any type described herein.

The invention will now be further described with reference to the drawings, wherein.

Figure 1:
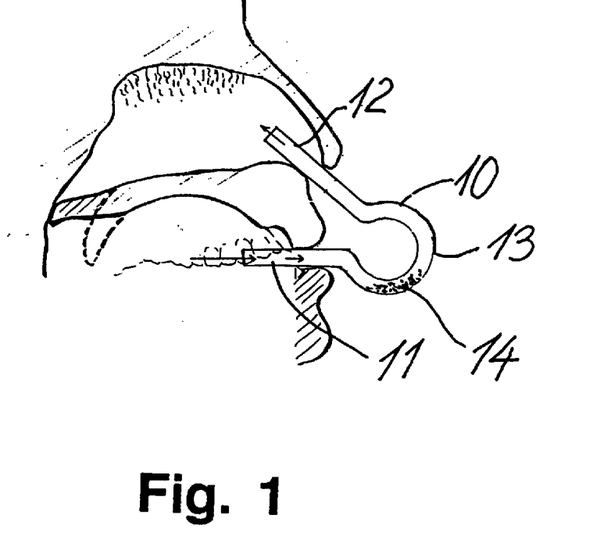
FIGS. 1–3 illustrate the use of three different embodiments of the device according to the invention.

FIG. 1 illustrates how a device according to the invention may be used for introducing a dose of a powdered or particulate substance into a nostril of the user. The device 10 shown in FIG. 1 is a tubular body, which may be formed integrally from rubber, cellulose material, glass or plastic, for example by blow moulding. The device is preferably of the disposable type and comprises at opposite ends a mouthpiece 11 to be inserted between the lips of the user and a nasal piece 12 to be inserted into a nostril of the user, respectively. The mouthpiece 11 and the nasal piece 12 are interconnected by an intermediate part 13. In the embodiment shown in FIG. 1, the intermediate part is formed substantially as an arc of a circle.

The tubular body forming the device 10 may have any suitable cross-sectional shape. When the cross-sectional shape is circular, the inner diameter may, for example, be 3–8 mm. The tubular device 10 may contain a dose 14 of a powdered or particulate substance. Prior to use of the device, the opposite open ends of the tubular body are closed by a pair of removable caps or any other type of closure means, which may be punctured or removed.

When the device shown in FIG. 1 is to be used, the closure means are removed from the opposite ends of the tubular device. Thereafter, the mouthpiece 11 and the nasal piece 12 are inserted between the lips and into a nostril of the user, respectively, as shown in FIG. 1. Now the user blows through the mouthpiece 11 whereby the powdered substance 14 is dispersed in the air flowing through the tubular device and is transferred to the nostril.

Figure 2:
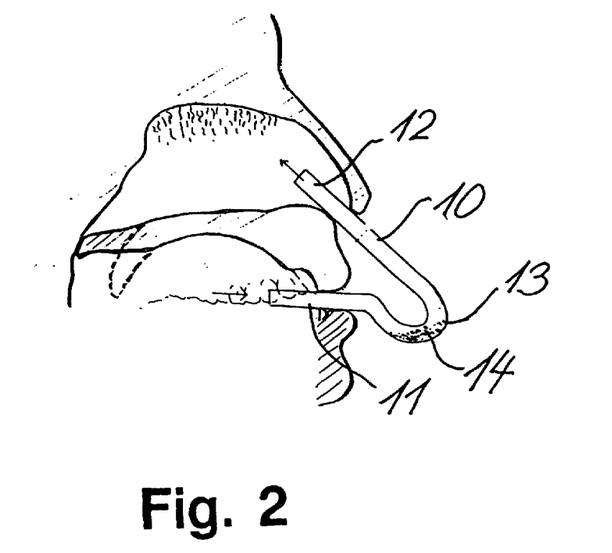

The tubular device 10 shown in FIG. 2 is similar to that shown in FIG. 1, but the intermediate part 13 is shaped differently. It should be understood that this intermediate part may have any other suitable shape.

Figure 3:
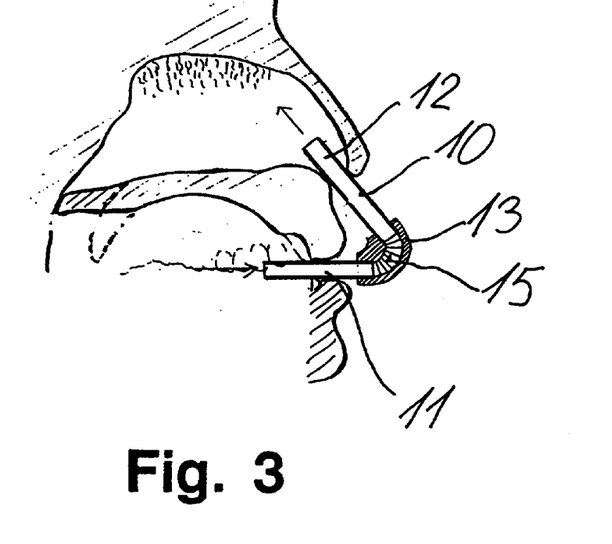
Figure 4:
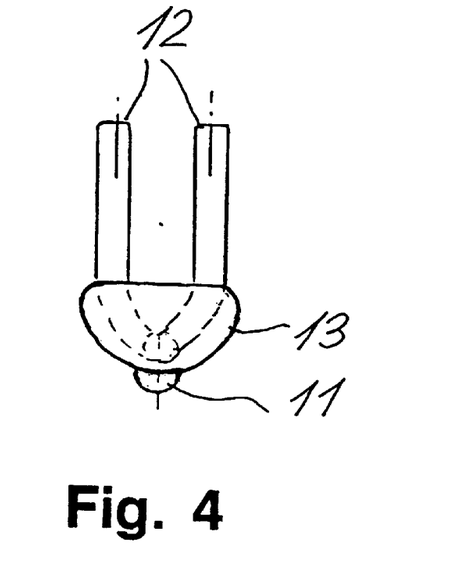
FIG. 4 is an enlarged side view of the device shown in FIG. 3, FIGS. 5–8 illustrate further embodiments of the device according to the invention
Figure 5:
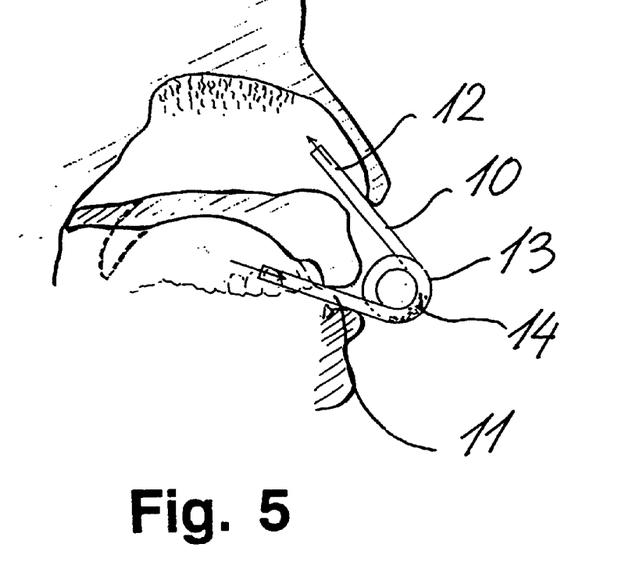

FIGS. 3 and 4 illustrate an embodiment of the device according to the invention which is composed by more parts. Thus, in FIGS. 3 and 4, the intermediate part 13 defines an inner cavity 15 opening into sockets for receiving the separately formed mouthpiece 11 and nasal piece or pieces 12, respectively. The intermediate part 13 shown in FIGS. 3 and 4 may be formed from plastic material by blow moulding and the mouthpiece 11 and the nasal piece or pieces 12 may be straight tube lengths made from glass or plastic material. As these tube lengths are interchangeably mounted in the intermediate part 13, they are preferably disposable while the intermediate part may be reused.

As shown in FIG. 4, the device may comprise a pair of nasal pieces 12 and a single mouthpiece 11. Alternatively, the device may comprise only one nasal piece. The inner cavity 15 of the intermediate part 13 is preferably shaped so as to create turbulence in the air flowing through the cavity so as to improve dispersion of the powdered or particulate substance into the air flowing through the tubular device when used.

The tubular device shown in FIG. 5 is formed integrally, for example from glass or plastic, and is of the disposable type containing a dose 14 of a particulate or powdered substance. Therefore, prior to use the opposite ends of the tubular body 10 is closed by caps or other removable closure means (not shown) as explained above. In FIG. 5, the intermediate part 13 has a helical shape with one or more turns or windings so as to improve dispersion of the powdered substance into air flowing through the tubular device 10 when used.

FIG. 6 shows the embodiment of the tubular device 10 according to the invention, which has a shape similar to a drinking straw. The device comprises opposite, substantially rectilinear end portions forming the mouthpiece 11 and the nasal piece 12, respectively. These rectilinear end portions are interconnected by an integrally formed intermediate part 13 with a plurality of peripherally extending corrugations, preferably of the type having relatively sharp peaks and valleys. Because of these corrugations, the intermediate part is bendable and the corrugations also causing turbulence in air flowing through the tubular device. Thereby dispersion of the powdered or particulate substance in the air flow is improved as previously explained. Prior to use, the tubular device may contain a dose 14 of substance, and the opposite ends of the device may be closed as explained above.

The tubular device 10 according to the invention, preferably comprise turbulence creating means in order to improve dispersion of the powdered or particulate substance in air flowing through the device. FIG. 7 shows an embodiment in which a helical thread member 16 made for example from metal or plastic has been arranged within the tubular device. The thread member may extend along any part of the length of the tubular member. In FIG. 7, the thread member 16 extend along substantially the total length of the device 10. The tubular member may, for example, by made from flexible film material, such as plastic film. The opposite ends of the tubular member may then be closed by heat sealing. Prior to use the sealed opposite ends of the tubular body have to be cut off.

Figure 8:
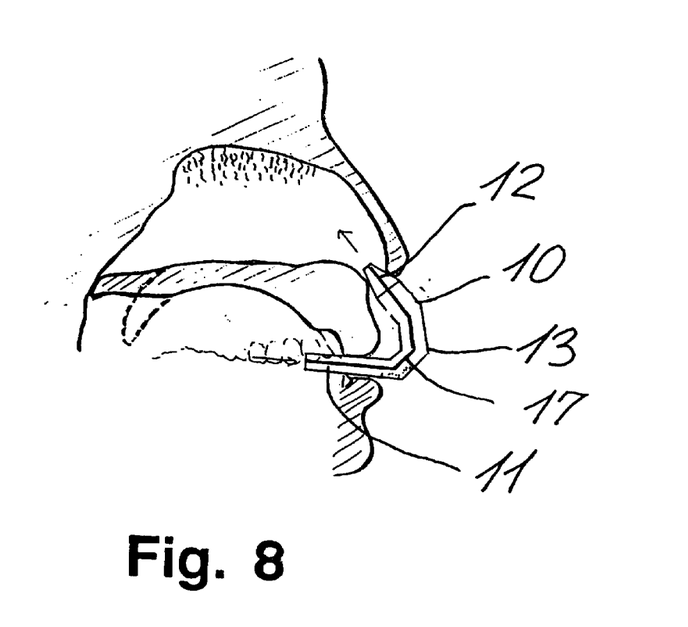
Figure 9:
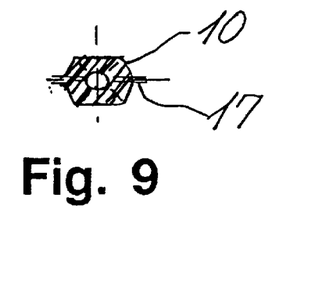
FIG. 9 is a cross-section of the device in FIG. 8 shown in an enlarged scale.

The tubular device 10 may be made by any suitable method of production. Even though extrusion is preferred because it is relatively cheap, vacuum forming may also be used. FIGS. 8 and 9 show an embodiment which has been made by heat welding a pair of separately vacuum formed parts together along opposite longitudinally extending seams 17.

Figure 10:
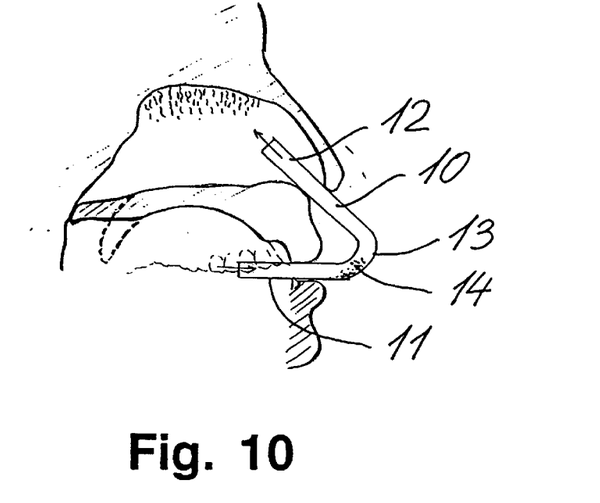
FIGS. 10 and 11 illustrate two further embodiments of the device according to the invention.

The embodiment shown in FIG. 10 may be made from a relatively stiff material, such as plastic or glass, with the shape shown from a deformable material, such as soft plastic or rubber. In the latter case, the tubular device may be formed by extrusion as a substantially straight tube length which is bent to the shape shown prior to use.

The embodiment shown in FIG. 10 may be made from a relatively stiff material, such as plastic or glass, with the shape shown or from a deformable material, such as soft plastic or rubber. In the latter case the tubular device may be formed by extrusion as a substantially straight tube length which is bent to the shape shown prior to use.

Figure 11:
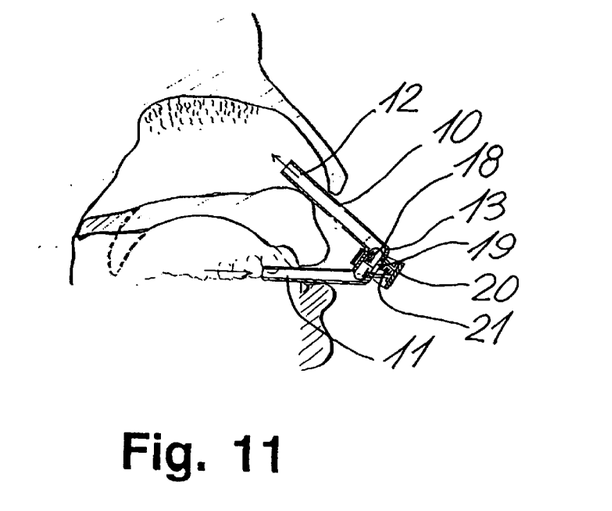

FIG. 11 shows an embodiment intended to be used several times. The tubular device 10 which may be made by blow moulding is divided into two parts which comprise the mouthpiece 11 and the nasal piece 12, respectively. These two parts may be hinged together or telescopically interconnected so that a capsule 18 containing a dose of the powdered or particulate substance may be inserted into the intermediate part 13. The device may contain piercing needles or a knife (not shown) which automatically opens the capsule when the two separate parts are closed. In the embodiment shown in FIG. 11 an opening 19 for inserting the capsule 18 is formed in the walls of the intermediate part 13. The intermediate part 13 is surrounded by a cover member 20 which may be rotated around the intermediate part between a position in which the opening 19 is exposed, and a position in which the opening is closed. A spring actuated piercing or cutting member 21 may automatically open the capsule 18, when the cover member has been moved to its closing position.

Figure 12:
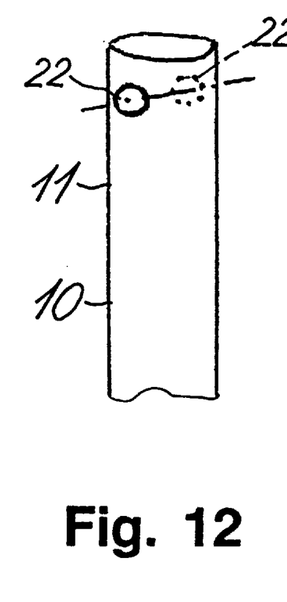
FIG. 12 shows in an enlarged scale a side view of an embodiment of the mouthpiece of the device according to the invention provided with venting openings.

FIGS. 12–17 diagrammatically illustrate various embodiments of the outer free end of the mouthpiece 11. In FIG. 12 a pair of diagrammatically oppositely arranged openings 22 are formed in the wall of the mouthpiece closely adjacent to the free end of the mouthpiece 11. If a person or patient inadvertently exhales into or inhales through the open end of the mouthpiece 11 when preparing the device for use, the respiratory air flowing through the open end of the mouthpiece 11 may pass through the openings 22. However, when the user has placed the free end of the mouthpiece 11 between the lips so that the openings 22 are covered or located inside the oral cavity and is blowing forcefully the openings 22 will not influence the air flow through the inner cavity of the tubular body 10.

Figure 13:
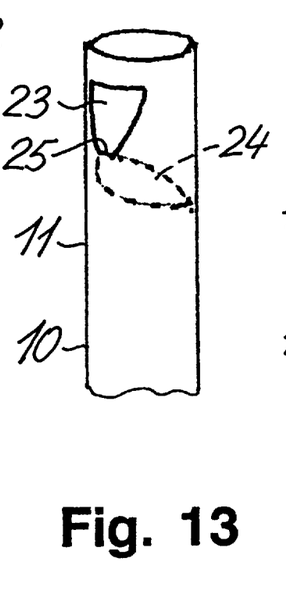
FIG. 13 shows another embodiment of the mouthpiece which has a venting opening and a flap extending into the inner cavity of the mouthpiece.

FIG. 13 illustrates an embodiment in which an opening 23 has been formed by cutting a flap 24 from the wall of the mouthpiece 11 such that the flap 24 is still connected to the wall of the tubular member via a hinge part 25 at the inner end of the opening 23. The flap 24 has been bent into the tubular member so as to extend across the inner cavity of the tubular member and partly restrict the passage therethrough. If a user inhales or exhales slightly through the open end of the mouthpiece 11 this will be of no or little effect because of the opening 23 and the flap 24. However, when the user has placed the free end of the mouthpiece between the lips and blows forcefully into the open end of the mouthpiece, the flap 24 will suddenly yield and open the flow passage through the tubular body 10. This creates a heavy pressure pulse such that the powdered or particulate product 14 is efficiently dispersed in the airflow and blown into the nostril of the user.

Figure 14:
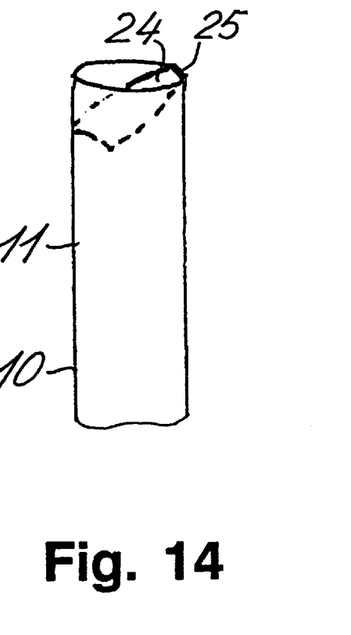
FIG. 14 is an embodiment of the mouthpiece with a flap extending from the free edge of the mouthpiece.

In the embodiment in FIG. 14 the flap 24 is connected to the mouthpiece 11 via a hinge part 25 located at the free edge of the mouthpiece 11. Otherwise, the embodiment shown in FIG. 14 functions substantially as that illustrated in FIG. 13.

Figure 15:
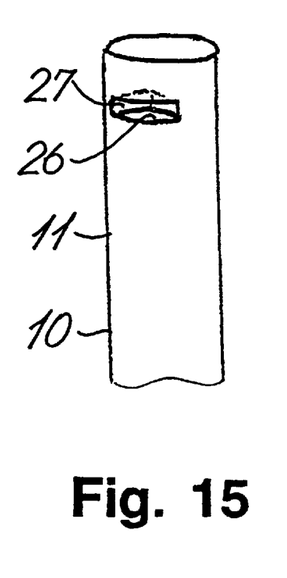
FIG. 15 shows a further embodiment of the mouthpiece having a venting opening and a tube wall part extending into the inner cavity of the mouthpiece.

FIG. 15 shows an embodiment in which a venting opening 26 has been formed in the mouthpiece 11 by cutting a pair of spaced, parallel slits in the mouthpiece wall and by pushing a strip-like wall part 27 defined between the slits inwardly into the inner cavity of the mouthpiece 11. Thus, the wall part 27 forms a flow obstructing member. The embodiment shown in FIG. 15 functions in a similar way as the embodiment shown in FIGS. 13 and 14.

Figure 16:
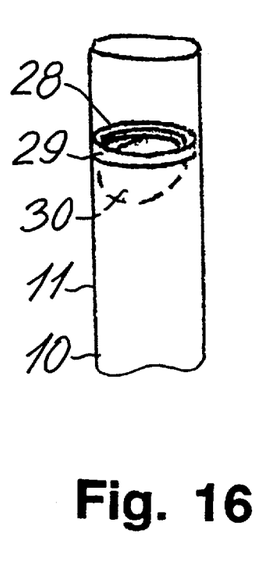
FIG. 16 is another embodiment of the mouthpiece containing a separate one-way valve.

FIG. 16 shows an embodiment in which a separate one-way valve 28 comprising an annular valve seat 29 and a flap-like moveable valve body 30 has been mounted within the mouthpiece 11 adjacent to the free end thereof. The one-way valve 28 prevents air from flowing through the tubular body 10 in the wrong direction if a patient by a mistake inhales through the tubular body 10 instead of blowing into the mouthpiece 11. Furthermore, the valve member 30 may be biassed towards its closed position by resilient forces such that the one-way valve opens only when a predetermined pressure difference has build up across the one-way valve 28.

Figure 17:
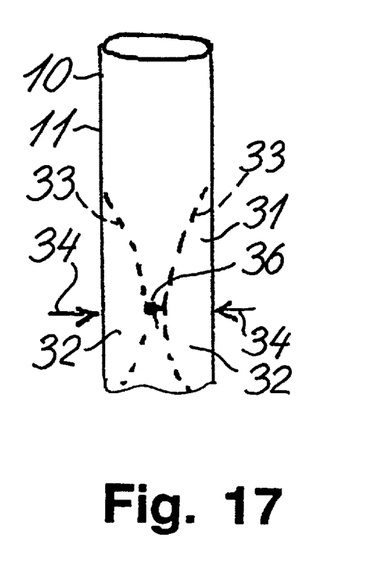
FIG. 17 shows an embodiment of the mouthpiece having inwardly deflatable wall parts.

FIG. 17 shows a mouthpiece 10 comprising a manually operateable valve 31. This manually operateable valve 31 is formed by oppositely arranged deformable wall parts 32 which may, for example, be defined by weakening lines or bending lines 33. When oppositely directed compressive forces indicated by arrows 34 in FIG. 17 are applied to the mouthpiece 11 by a pair of fingers 35 (vide FIG. 18) a restriction or gorge 36 is formed within the mouthpiece 11. This restriction 36 prevents unintentional airflow through the tubular body caused by unintentional suction or blowing action.

Figure 18:
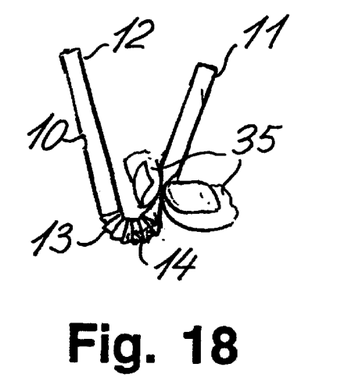
FIG. 18 is a side view illustrating how a device with a mouthpiece as shown in FIG. 17 is gripped by a user.
Figure 19:
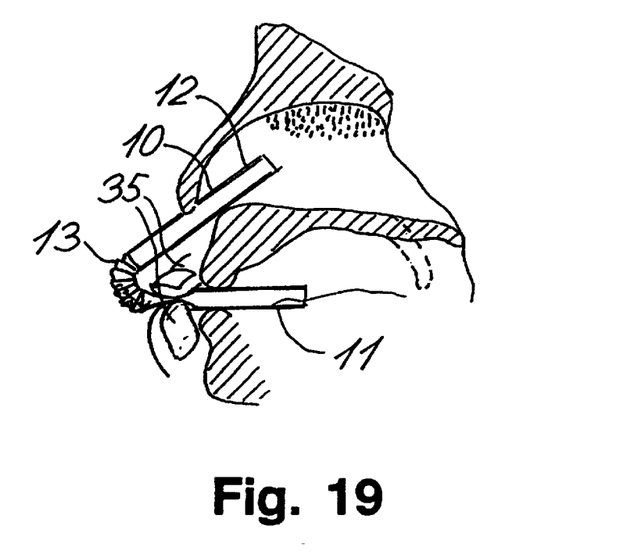
FIG. 19 illustrates how the device shown in FIG. 18 may be inserted into the nostril and between the lips of a user.
Figure 20:
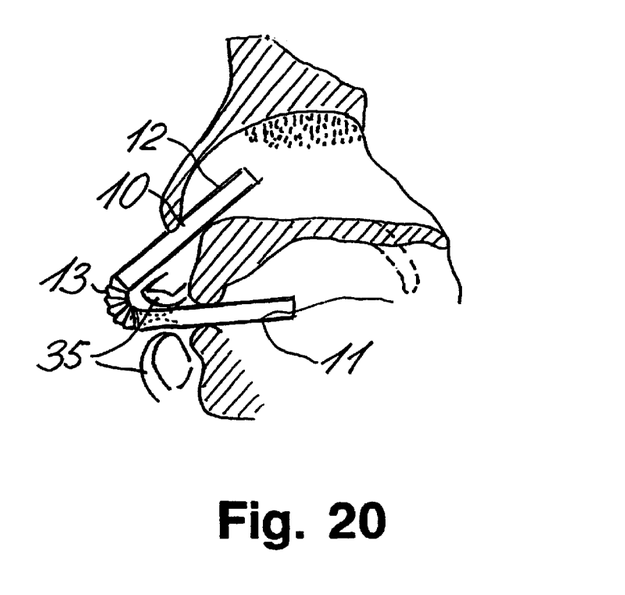
FIG. 20 shows the same as FIG. 19, but when the user blows through the mouthpiece.

When a device 10 according to the invention having a mouthpiece 11 as that illustrated in FIG. 17 is to be used the deformable wall parts 32 of the device are gripped between a pair of fingers 35 as illustrated in FIG. 18 so as to form a restriction 36. Thereafter the mouthpiece 11 and the nasal piece 12 are positioned between the lips and in the nostril of the user, respectively, as illustrated in FIG. 19, while the deformable parts 32 are still compressed. When the user is blowing forcefully into the mouthpiece 11 the deformable parts 32 are released as illustrated in FIG. 20. The pressure having been built up at the entrance of the mouthpiece 10 is sufficient to suddenly inflate the deformed wall parts 32 so that they are returned to their starting position. A sudden forceful flow of air through the tubular device 10 is thereby created. The dose 14 of powdered or particulate product is then dispersed into and entrained by the airflow, whereby the powdered or particulate substance is transferred to the nostril.

EXAMPLE

The deposition patterns and clearance characteristics of a powdered substance after administration from two differing devices were evaluated.

Introduction

Figure 6:
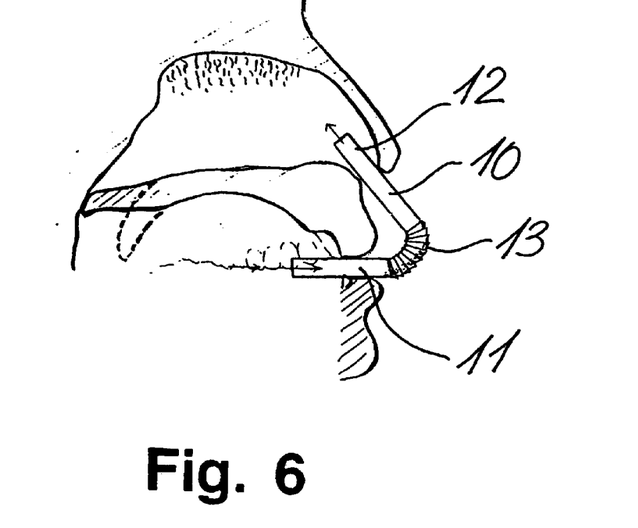
Figure 7:
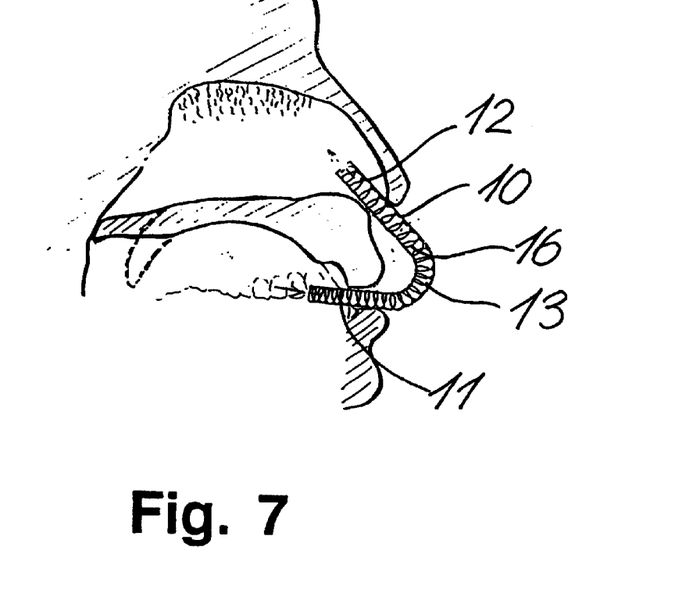

The time taken for a formulation to be cleared from the nose can be altered by depositing the formulations into different regions of the nose. The tip of the nose is a non-ciliated region, hence, drugs that are delivered to the tip of the nose will remain in the nasal cavity for longer periods of time compared to those administered to the respiratory or olfactory regions of the nose. It is possible that the use of differing administration devices could produce vastly different clearance times for the same drug formulations. In this example an embodiment of the device according to the invention as that shown in FIG. 6 (in the following called the "Invention Device") was compared with a conventional device for nasal delivery of dry powder (in the following called the "State of Art" with reference to the nasal cycle.

The nasal cycle is a well recognised phenomenon that produces rhythmical alteration of unilateral nasal resistance and airflow. To effectively investigate nasal drug delivery it is important to acquire information on the nasal cycle of each volunteer since the nasal cycle may have an effect on mocociliarily clearance.

Methods

In order to study the clearance characteristics and deposition patters produced by the differing administration devices radiolabelled powder were administered to a group of six healthy human volunteers according to a cross over design on two study days with one week between each treatment. Before administration each volunteer performed measurements of peak nasal inspiratory flow from each nostril. The data gained was used to map the cyclical rhythm of each volunteer, enabling the administration of the formulations into a patent nostril.

State of Art

The volunteers took two deep breathes through the nostril whilst holding the device in the tip of the patent nostril. The contents of the device (10 mg, approximately 1 Msq) was delivered to the mucosal surface of the patent nostril.

Invention

The volunteers placed the long leg of the device into the tip of the nose and closed their mouth around the shorter leg. One quick, sharp blow delivered the contents of the device (10 mg, approximately 1 Mbq) to the mucosal surface of the patent nostril.

The deposition and subsequent clearance of the different nasal delivery systems was followed by gamma scintigraphy, using a Maxi Camera II Gamma Camera (General Electric). The position of the nose of the volunteer was fixed on the collimator of the gamma camera using a specially designed template. Static lateral views (60 seconds duration) were taken directly after dosing and at appropriate time intervals for 180 minutes after administration. The images were recorded for subsequent analysis and quantification.

Results

Quantification of the data from the volunteers involved defining regions of interest around the nasal cavity and throat. The count rate from each region of interest (ROI), corrected for radioactive decay and background, was then expressed as a proportion of the highest one minute count rate, typically the image recorded in the nasal cavity ROI immediately after dosing. That is, the highest count rate was assigned a 100% value, which was then used to calculate the % values for the outer time point count rates.

In this way the clearance of the formulations from the nasal cavity was evaluated as a decrease in percentage activity against time for each volunteer. Using this clearance data, the time taken for 50% of the formulation to be cleared from the nasal cavity ROI was calculated for each volunteer. In addition, the deposition patterns produced by the device were evaluated by defining an area of interest around the initial site of deposition and counting the computer cells covered.

| Volunteer Identification | State of Art | | Invention Device | |
| --- | --- | --- | --- | --- |
| | $T_{50}$ (min) | Deposition area (cells) | $T_{50}$ (min) | Deposition area (cells) |
| 001 | 170 | 41 | 158 | 35 |
| 004 | 43 | 48 | 171 | 56 |
| 005 | 123 | 37 | 153 | 29 |
| 007 | 84 | 36 | 101 | 28 |
| 009 | 110 | 34 | 139 | 25 |
| 010 | 144 | 36 | 48 | 27 |
| Average | 112 | 39 | 128 | 33 |
| SE± | ±18 | ±2 | ±18 | ±5 |

Conclusions/Observations

The Invention Device and the State of Art have produced clearance times and areas of deposition that are not significantly different from one another.

The Invention devices emptied very well, only one sharp blow of air was required to completely empty the devices. In comparison, the State of Art often required two intakes of breath to administer all of the contents.

It is believed that the Invention Device will require a simple flow valve to be completely effective. The devices empty so well that once the long leg is placed in the nostril any intake of breath around the short leg is enough to cause the device to empty the wrong way into the mouth.

The volunteers reported less mucosal irritation after the use of the Invention Devices.

It should be understood that various other embodiments could be made within the scope of the present invention. Thus, any of the features disclosed in connection with the embodiments shown in the drawings could be interchanged or combined in any suitable manner.

What is claimed is:

1. A device for applying a powdered or particulate substance to a mucous membrane within a nostril of a user of the device, said device comprising:

a tubular body having:
an intermediate bend and/or bendable section composed of adjacent, peripherally extending corrugations with the corrugations having a substantially serrated outline when viewed in a longitudinal axial section, the tubular body defining
an inner flow passage with a cross-sectional area not exceeding 75 mm² extending longitudinally between a nasal piece at a first end of the tubular body to be inserted into the nostril of the user and an opposite second end of said body,
wherein the second end of the tubular body defines a mouthpiece to be inserted between the lips of the user, the length and the shape of the tubular body being such that the nasal piece and the mouthpiece may at the same time be positioned into the nostril and between the lips, respectively, of the user, whereby the user may blow into the mouthpiece end of the flow passage and transfer powdered or particulate substance arranged within the flow passage of the tubular body to the nostril in a dispensed condition.

2. A device according to claim 1, further comprising:

a dose of a powdered or particulate substance arranged within the flow passage.

3. A device according to claim 2, wherein the powdered or particulate substance is as substance active against allergy.

4. A device according to claim 1, wherein the cross-sectional areas of the flow passage do not exceed 70 mm$^2$.

5. A device according to claim 4, wherein the cross-sectional areas of the flow passage do not exceed 50 mm$^2$.

6. A device according to claim 5, wherein the cross-sectional areas of the flow passage are 7–35 mm$^2$.

7. A device according to claim 6, wherein the cross-sectional areas of the flow passage are about 20 mm$^2$.

8. A device for applying a powdered or particulate substance to a mucous membrane within a nostril of a user of the device, said device comprising:

a tubular body having:

a mouthpiece at a first end to be inserted between the lips of the user; and a nasal piece at an opposite second end to be inserted into the nostril, with the tubular body further defining:

an inner flow passage extending longitudinally between the mouthpiece and the nasal piece, whereby the user may blow into the mouthpiece end of the flow passage and transfer the powdered or particulate substance arranged within the flow passage of the tubular body to the nostril in a dispensed condition;

wherein the tubular body also comprises:

an intermediate bent and/or bendable section wherein the bent and/or bendable section comprises:

adjacent, peripherally extending corrugations, said corrugations having a substantially serrated outline when viewed in a longitudinal, axial section, the flow passage of the tubular body having a cross-sectional area not exceeding 75 mm$^2$;

wherein said device further comprises:

restriction means.

* * * * *